(12) United States Patent
Marnfeldt

(10) Patent No.: US 7,330,756 B2
(45) Date of Patent: Feb. 12, 2008

(54) IMPLANTABLE MICROSTIMULATOR WITH CONDUCTIVE PLASTIC ELECTRODE AND METHODS OF MANUFACTURE AND USE

(75) Inventor: Goran Nils Marnfeldt, Hollviken (SE)

(73) Assignee: Advanced Bionics Corporation, Valencia, CA (US)

( * ) Notice: Subject to any disclaimer, the term of this patent is extended or adjusted under 35 U.S.C. 154(b) by 272 days.

(21) Appl. No.: 11/084,368

(22) Filed: Mar. 18, 2005

(65) Prior Publication Data

US 2006/0212075 A1 Sep. 21, 2006

(51) Int. Cl.
*A61N 1/00* (2006.01)
*A61N 1/02* (2006.01)
*A61N 1/05* (2006.01)
*A61N 1/375* (2006.01)

(52) U.S. Cl. .................. 607/2; 607/36; 607/116; 600/372; 600/395

(58) Field of Classification Search .............. 607/2, 607/36, 116
See application file for complete search history.

(56) References Cited

U.S. PATENT DOCUMENTS

| | | | | |
|---|---|---|---|---|
| 4,281,668 A * | 8/1981 | Richter et al. | ............... | 607/121 |
| 4,685,467 A * | 8/1987 | Cartmell et al. | ............ | 600/385 |
| 5,193,539 A | 3/1993 | Schulman et al. | | |
| 5,193,540 A | 3/1993 | Schulman et al. | | |
| 5,312,439 A | 5/1994 | Loeb | | |
| 5,782,761 A * | 7/1998 | Gusakov | ..................... | 600/391 |
| 6,051,017 A | 4/2000 | Loeb et al. | | |
| 6,609,032 B1 | 8/2003 | Woods et al. | | |
| 6,708,051 B1 * | 3/2004 | Durousseau | ................ | 600/383 |
| 2004/0059392 A1 | 3/2004 | Parramon et al. | | |

FOREIGN PATENT DOCUMENTS

| | | |
|---|---|---|
| WO | WO 98/37926 | 9/1998 |
| WO | WO 98/43700 | 10/1998 |
| WO | WO 98/43701 | 10/1998 |

OTHER PUBLICATIONS

U.S. Appl. No. 11/040,209, Colvin et al., unpublished.
U.S. Appl. No. 11/056,762, He, T. X., unpublished.

* cited by examiner

*Primary Examiner*—Kennedy J. Schaetzle
*Assistant Examiner*—Yun Haeng Lee
(74) *Attorney, Agent, or Firm*—Darby & Darby P.C.; Bruce E. Black

(57) ABSTRACT

An implantable microstimulator includes a plastic housing having a first end; an electronic subassembly; and a conductive plastic electrode disposed at the first end of the plastic housing and in electrical communication with the electronic subassembly. The microstimulator forms a hermetically sealed structure. Optionally, the microstimulator also includes a second electrode disposed at a second end of the plastic housing and in electrical communication with the electronic subassembly. The second electrode may also be a conductive plastic electrode.

19 Claims, 2 Drawing Sheets

IMPLANTABLE MICROSTIMULATOR WITH CONDUCTIVE PLASTIC ELECTRODE AND METHODS OF MANUFACTURE AND USE

FIELD

The invention is directed to implantable microstimulators with one or more conductive plastic electrodes and methods of using the devices. In addition, the invention is directed to implantable microstimulators with conductive plastic electrodes and a plastic housing and methods of using the devices.

BACKGROUND

Implantable microstimulators have been developed to provide therapy for a variety of disorders, as well as other treatments. For example, implantable microstimulators can be used in neurological therapy by stimulating nerves or muscles, for urinary urge incontinence by stimulating nerve fibers proximal to the pudendal nerves of the pelvic floor, for erectile and other sexual dysfunctions by stimulating the cavernous nerve(s), for reduction of pressure sores or venous stasis, etc.

Implantable microstimulators, such as the BION® device (available from Advanced Bionics Corporation, Sylmar, Calif.), have exposed electrodes and a small, often cylindrical, housing that contains the electronic circuitry and power source that produce electrical pulses at the electrodes for stimulation of the neighboring tissue. It is preferable that the electronic circuitry and power source be held within the housing in a hermetically-sealed environment for the protection of the user and the protection of the circuitry and power source. Once implanted, it is often preferable that the microstimulator can be controlled and/or that the electrical source can be charged without removing the microstimulator from the implanted environment.

BRIEF SUMMARY

One embodiment is an implantable microstimulator that includes a plastic housing having a first end; an electronic subassembly; and a conductive plastic electrode disposed at the first end of the plastic housing and in electrical communication with the electronic subassembly. The microstimulator forms a hermetically sealed structure. Optionally, the microstimulator also includes a second electrode disposed at a second end of the plastic housing and in electrical communication with the electronic subassembly. The second electrode may also be a conductive plastic electrode.

Another embodiment is a method of making a microstimulator. A plastic housing is formed with a first end. A conductive plastic electrode is formed and coupled to the first end of the plastic housing. An electronic subassembly is disposed within the plastic housing. Optionally, a second electrode is disposed at a second end of the plastic housing. Optionally, the plastic housing and the conductive plastic electrode (and, optionally, a second electrode) can be formed together by, for example, injection molding such as dual material injection molding.

Yet another embodiment is a method of treating body tissue. The microstimulator described above is implanted into a body and the microstimulator is operated to stimulate the body tissue using the first electrode and, optionally, a second electrode.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable microstimulators with conductive plastic electrodes and methods of using the devices. In addition, the invention is directed to implantable microstimulators with conductive plastic electrodes and a plastic housing and methods of using the devices.

Previously, implantable microstimulators have been made using housings and electrodes of metal (for example, titanium) and ceramic components. Examples of such microstimulators are found in U.S. Pat. Nos. 5,139,539; 5,239,540; 5,312,439; 6,051,017; and 6,609,032; U.S. Patent Application Publication No. 2004/059392; and PCT Patent Applications Publication Nos. 98/37926; 98/43700; and 98/43701, all of which are incorporated herein by reference. The manufacture of such microstimulators typically includes brazing steps to couple the metal and ceramic components together to form a hermetically-sealed device. Microstimulators made using a plastic housing are described in U.S. patent application Ser. No. 11/040,209, incorporated herein by reference.

An implantable microstimulator can be formed using a plastic housing and at least one conductive plastic electrode attached to the plastic housing. The plastic housing and electrodes can form a hermetically-sealed device. In at least one embodiment, the plastic housing and conductive plastic electrode(s) can be formed together using, for example, a molding technique such as dual material injection molding. In this manner, a seamless junction between the plastic housing and the conductive plastic electrode(s) can be formed to facilitate the manufacture of a hermetically-sealed device.

In at least some embodiments, the implantable microstimulator with plastic housing and conductive plastic electrode(s) can be easier or less costly to manufacture, or there can be a reduction in the time, manpower, or skill used to manufacture the device, when compared to earlier implantable microstimulators. In particular, the implantable microstimulator with plastic housing and conductive plastic electrode(s) typically does not involve brazing operations. In addition, the plastic housing may be more permeable to RF signals than metal or ceramic. These RF signals can be used to charge a battery in the housing or to provide data or instructions to a processor disposed in the housing.

Figure 1:
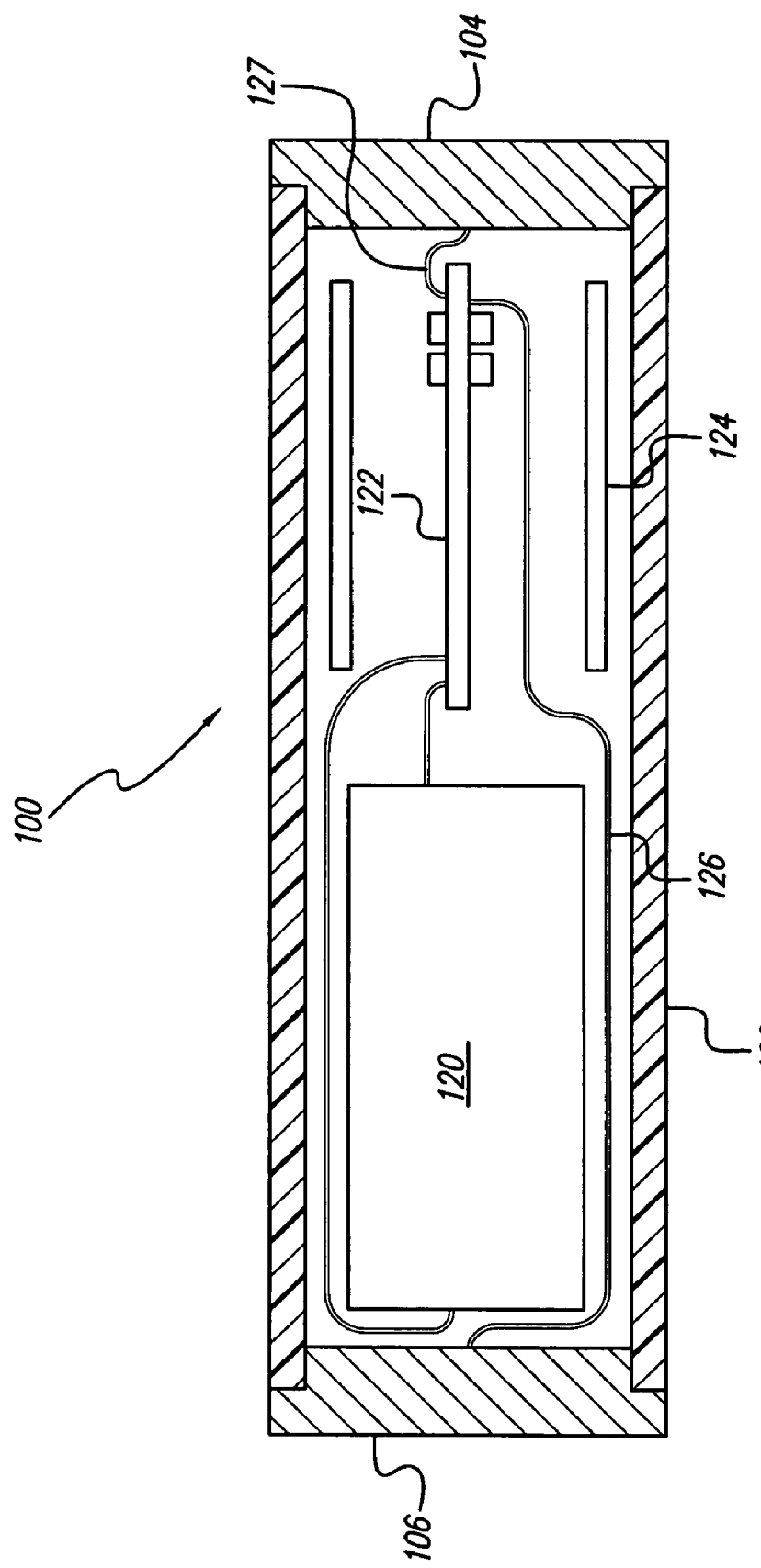
FIG. 1 is a cross-sectional view of one embodiment of a microstimulator, according to the invention.

FIG. 1 illustrates one embodiment of an implantable microstimulator 100. The implantable microstimulator 100 includes a plastic housing 102, a conductive plastic electrode 104, a second electrode 106 (which may or may not be formed using conductive plastic), a power source 120, an electronics subassembly 122, and an optional antenna 124. Other embodiments of an implantable microstimulator may include more or fewer components. It will be understood that the power source 120 and/or components of the electronics subassembly 122 and/or the optional antenna 124 can be provided outside of the housing in a separate unit and coupled to the implantable microstimulator by a lead. Examples of such arrangements are described in U.S. patent application Ser. No. 11/056,762, incorporated herein by reference.

The plastic housing 102 can be formed of a plastic material that resists the transport of moisture into the interior of the housing and is sufficiently sturdy to protect the components on the interior of the housing from damage under expected implantation and usage conditions. Preferably, the material of the plastic housing is a hydrophobic polymer material. The plastic material of the housing can be a homopolymer, a copolymer formed using two or more different monomeric units, or a mixture of polymers or other materials. Examples of suitable polymer materials include polyolefins, polypropylene homopolymers and copolymers, teflon, and polyetheretherketone (PEEK). The plastic housing may also include additives such as, for example, fillers, plasticizers, antioxidants, colorants, and the like.

The thickness of the walls of the plastic housing may also impact the moisture permeability of the plastic housing. A minimum thickness needed to achieve a particular degree of resistance to moisture transport will often depend on the material selected for the housing, as well as any additives. In general, however, the thickness of the walls of the plastic housing is at least 100 μm and typically ranges from 50 to 10,000 μm.

The plastic housing can have any shape including, for example, cylindrical, conical, parallelepiped, cubic, and the like. In at least some embodiments, a cylindrical shape is preferred. The lateral cross-sectional dimensions can be the same or can vary along the length of the plastic housing. In one embodiment, the plastic housing has a cylindrical shape with a uniform diameter along the length of the plastic housing. The uniform diameter can be, for example, no greater then 5 mm, no greater than 4 mm, no greater than 3.3 mm, or no greater than 3 mm. This uniform diameter can be in the range of from, for example, 1 to 5 mm. In another embodiment, the plastic housing is a cylinder that is wider at the ends and narrower in the middle or the plastic housing is a cylinder that is wider in the middle and narrower at the ends.

Optionally, the plastic housing can be covered, in full or in part, with a coating. The coating can be provided to improve or alter one or more properties of the plastic housing including, for example, biocompatibility, hydrophobicity, moisture permeability, leaching of material into or out of the plastic housing, and the like. The optional coating can be a polymer material, inorganic material, or organic material. As an example, the plastic housing may be coated with an inorganic material, such as, for example, silicon dioxide, silicon nitride, titanium dioxide, or the like, to reduce moisture permeability. As another example, a silicone coating may be used to improve biocompatibility. In yet another example, a coating can be applied which contains a compound, such as, for example, a drug, prodrug, hormone, or other bioactive molecule, that can be released over time when the microstimulator is implanted. (In another embodiment, the plastic housing itself may include such a compound to be released over time after implantation.) In some embodiments, the coating includes two or more layers of the same or different materials. For example, alternating layers of inorganic materials can be deposited as a coating to improve resistance to moisture transport through the plastic housing.

The formation of the coating can be accomplished using any method including, for example, dip-coating, sputtering, reactive sputtering, physical or chemical vapor deposition, spray coating, and the like. The coating can be applied before the other microstimulator components have been assembled with the plastic housing or at any other point in the microstimulator manufacturing process including applying the coating after the microstimulator has been completely assembled. Typically, the coating is non-conductive.

The electrodes 104, 106 typically form the anode and cathode of the microstimulator. The conductive plastic electrode 106 (and, optionally, the second electrode 104) can be formed of a plastic material that resists the transport of moisture into the interior of the housing and is sufficiently sturdy to protect the components on the interior of the housing from damage under expected implantation and usage conditions. Preferably, the material of the conductive plastic electrode 106 (and, optionally, the second electrode 104) is a hydrophobic polymer material. The plastic material of the conductive plastic electrode 106 (and, optionally, the second electrode 104) can be a homopolymer, a copolymer formed using two or more different monomeric units, or a mixture of polymers or other materials.

The conductive plastic electrode 104 is formed using a conductive plastic, such as a conductive polymer material or a polymer material with a conductive material dispersed therein. Examples of conductive polymers include polyaniline, polypyrrole, poly(p-phenylene-vinylene)s, and the like. Typically, the selected polymer material is biocompatible and appropriate for implantation. Examples of conductive materials suitable for dispersing in a non-conductive or conductive polymer material include metal, alloy, and carbon particles, flakes, or fibers. Suitable non-conductive polymer materials for combination with a conductive material include all of those polymers described above for use in forming the plastic housing. One example of a conductive plastic formed using a combination of a non-conductive polymer material and a conductive material is polyetheretherketone (PEEK) with carbon fibers disposed therein. In one embodiment, the plastic housing, conductive plastic electrode, and second electrode are all metal-free.

The second electrode 106 can be formed of the same conductive material as the conductive plastic electrode 104 or a different conductive material. Examples of suitable materials for the second electrode include conductive plastics (such as those described above with respect to conductive plastic electrode 104), metals, alloys and other conductive materials. Examples of suitable metals and alloys include, but are not limited to, titanium, iridium, platinum, platinum/iridium alloy, stainless steel, and the like. The second electrode 106 can be formed entirely of a single conductive material, such as a conductive plastic, metal, or alloy, or one or both of the electrodes can be formed using a combination of conductive materials such as, for example, a conductive coating over a bulk metallic electrode. In other embodiments, the second electrode 106 can be formed from a polymeric material that is at least partially, or fully, coated with a conductive coating, such as a metal, alloy, or conductive oxide (e.g., iridium oxide) coating. Preferably, the second electrode 106 is formed of materials that do not substantially corrode under the operating conditions and in the operating environment for the expected lifetime of the microstimulator.

In one embodiment, the conductive plastic electrode 104 (and, optionally, the second electrode) is formed using the same polymer material as the plastic housing 102 except that the conductive plastic electrode (and, optionally, the second electrode) also includes a conductive material disposed in the polymer material. For example, the conductive plastic electrode 104, plastic housing 102 (and, optionally, the second electrode 106) are formed using PEEK. The conductive plastic electrode 104 (and, optionally, the second electrode 106) also include carbon fibers disposed in the PEEK.

In some embodiments, the plastic housing 102, the conductive plastic electrode 104, and, optionally, the second electrode 106 are formed together. For example, the plastic housing 102, the conductive plastic electrode 104, and, optionally, the second electrode 106 can be formed together using a molding technique such as dual material injection molding. Forming these components together can produce relatively seamless junctions between the plastic housing and one or both of the electrodes 104, 106.

In one embodiment, the conductive plastic electrode 104 and the plastic housing 102 are formed together. The electronic subassembly 122 and power source 120 can then be disposed in the housing and the second electrode 106 can then be coupled and sealed to the plastic housing to produce the microstimulator.

In another embodiment, the conductive plastic electrode 104, second electrode 106, and plastic housing 102 are formed together. The electronic subassembly 122 and power source 120 can be disposed in a mold and the electrodes 104, 106 and plastic housing 102 formed around those components. For example, the electronic subassembly 122 and, optionally, the power source 120 can be encased in a shell (not shown) with electrode conductors 126, 127 extending. The plastic housing 102 and electrodes 104, 106 can then be molded around shell, electronic subassembly, and power source with the conductors being in contact with the respective electrode.

Each of the electrodes 104, 106 can be a solid body at one end of the plastic housing. The electrode can be coupled to the battery and electronic subassembly by attaching a conductor 126, 127 to an interior surface of the electrode. As an alternative, the electrode 104 or 106 can include a hole (not shown) through the electrode body. A conductor 126, 127 from the electronic subassembly 122 or power source 120 can then be guided through the hole and the conductor can be attached to a conductive exterior surface of the electrode. The attachment of the conductor to the electrode can be performed by any method including, for example, soldering or laser welding. Generally, if a hole through the electrode body is utilized, the hole is also sealed prior to, simultaneously with, or after the attachment of the conductor to the electrode surface to maintain a hermetically-sealed environment within the plastic housing. Other methods and arrangements for attaching a conductor to each electrode can be used.

The electrodes 104, 106 may be positioned at ends of the plastic housing 102. In at least some embodiments, the electrodes 104, 106 are disposed at opposing or opposite ends of the plastic housing 102. For example, the electrodes 104, 106 can be disposed at opposite ends of a cylindrical plastic housing, as illustrated in FIG. 1.

The electrodes 104, 106 and plastic housing 102 are preferably coupled together to form a hermetically-sealed environment within the housing. As described above, one method of accomplishing this objective is to form the plastic housing and one or both of the electrodes together. In another embodiment, the interior portion of at least one end of the plastic housing 102 is threaded, as is the corresponding exterior surface of the second electrode 106 (and, optionally, the conductive plastic electrode 104), so that the electrode(s) can be screwed into the end(s) of the plastic housing. Optionally, an adhesive can be spread on either the interior portion of the housing or the exterior surface of the electrode(s) or both to further seal the plastic housing 102 and electrode(s). Preferably, the selected adhesive is moisture resistant and biocompatible.

Another option for enhancing the sealing of the electrode(s) to the plastic housing is to provide a solvent disposed on the surface of one or both of the electrodes 104, 106 and capable of at least partially dissolving or deforming the plastic material of the plastic housing 102 so that the plastic housing is solvent welded or otherwise better adhered or conformed to the electrode(s).

As yet another option, the ends of the plastic housing can be heated, ultrasonically or otherwise, for sealing of the plastic housing to the electrode(s). Heating may result in better conformation or bonding of the plastic housing to the electrode(s). Moreover, in an embodiment in which one or both of the electrodes are formed using a plastic material, heating may result in mixing, if desired, of the plastics of the housing and electrode(s) to improve bonding.

It will be understood that other methods of coupling the electrodes and plastic housing can be used. Such methods can include one or more of the following: adhesively attaching the electrode(s) to the housing; sliding at least a portion of the electrode(s) into the housing to form a compressive or frictional fit; screwing threaded interior surfaces of the electrode(s) onto threaded exterior surfaces of the plastic housing; coating a sealed end of the plastic housing (optionally with a hole extending through the housing for the conductor) with a conductive material to form an electrode or the like.

In at least some embodiments, the length of the combined plastic housing 102 and electrodes 104, 106 is no greater than 30 mm. Typically the length of the combined plastic housing 102 and electrodes 104, 106 is in the range of 10 to 30 mm.

A power source 120 can be disposed within the plastic housing 100. Any power source can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 124 or a secondary antenna. The external power source can be in a device that is mounted on the skin of the user or in a unit that is provided near the microstimulator user on a permanent or periodic basis.

If the power source 120 is a rechargeable battery, the battery may be recharged using the optional antenna 124, if desired. Power can be provided to the battery 120 for recharging by inductively coupling the battery through the antenna to a recharging unit 210 (see FIG. 5) external to the user. Examples of such arrangements can be found in the microstimulator references identified above.

Figure 2:
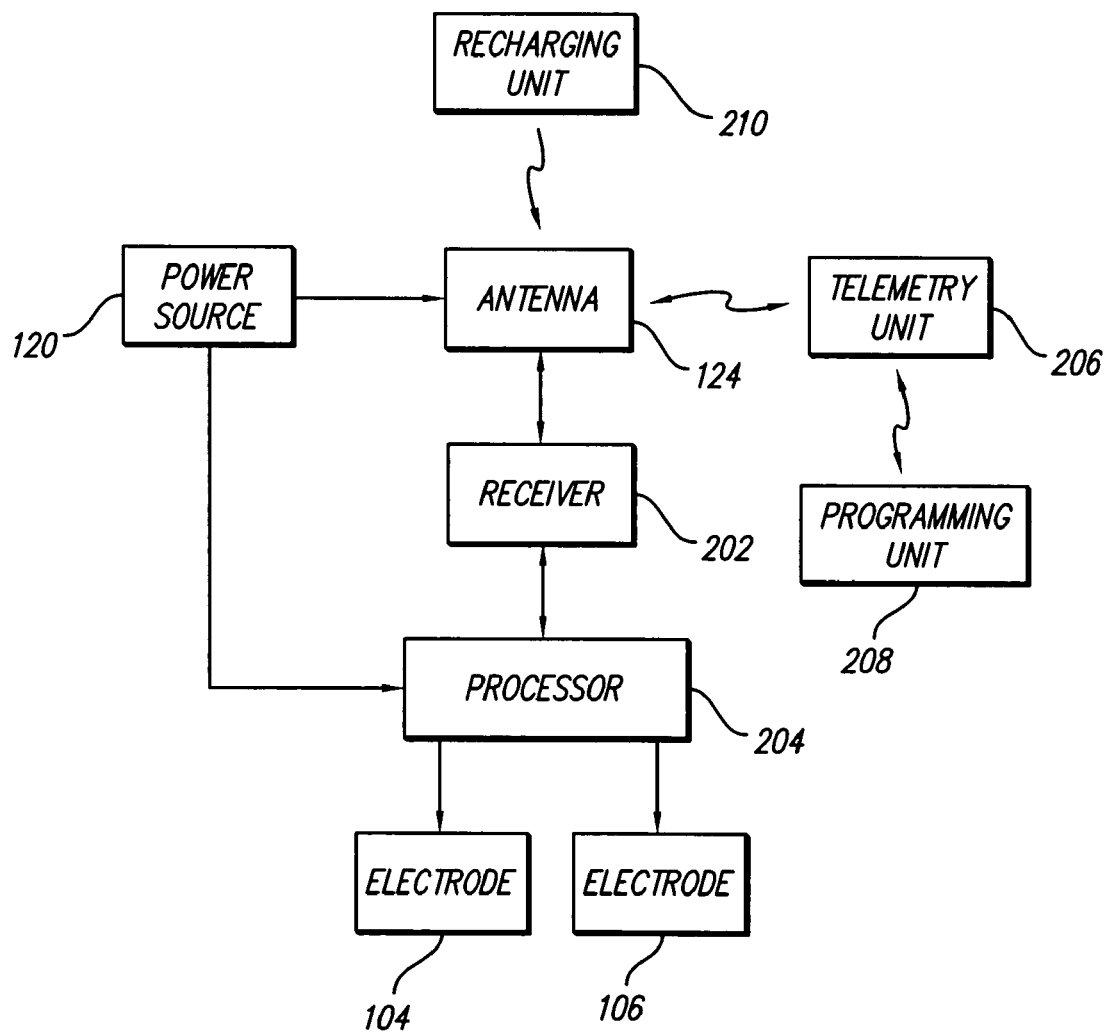
FIG. 2 is a schematic overview of components for a system for microstimulation of body tissues, according to the invention.

In one embodiment, electrical current is emitted by the electrodes 104, 106 to simulate motor nerve fibers, muscle fibers, or other body tissues near the microstimulator. The electronic subassembly 122 provides the electronics used to operate the microstimulator and generate the electrical pulses at the electrodes 104, 106 to produce stimulation of the body tissues. FIG. 2 illustrates one embodiment of components of the electronic subassembly and associated units. It will be understood that the electronic subassembly can include more, fewer, or different components and can have a variety of different configurations including those configurations disclosed in the microstimulator references cited above. Some or all of the components of the electronic subassembly can be positioned on one or more circuit boards or similar carriers within the plastic housing, if desired.

In the illustrated embodiment, a processor 204 is provided to control the timing and electrical characteristics of the microstimulator. For example, the processor can, if desired, control one or more of the timing, periodicity, strength, duration, and waveform of the pulses. Any processor can be used and can be as simple as a electronic device that produces pulses at a regular interval or the processor can be capable of receiving and interpreting instructions from an external programming unit 208 that allow modification of pulse characteristics. In the illustrated embodiment, the processor 204 is coupled to a receiver 202 which, in turn, is coupled to the optional antenna 124. This allows the processor to receive instructions from an external source to direct the pulse characteristics.

In one embodiment, the antenna 124 is capable of receiving signals (e.g., RF signals) from an external telemetry unit 206 which is programmed by a programming unit 208. The programming unit 208 can be external to, or part of, the telemetry unit 206. The telemetry unit 206 can be device that is worn on the skin of the user or can be carried by the user and can have a form similar to a pager or cellular phone, if desired. As another alternative, the telemetry unit may not be worn or carried by the user but may only be available at a home station or at a clinician's office. The programming unit 208 can be any unit that can provide information to the telemetry unit for transmission to the implanted microstimulator. The programming unit 208 can be part of the telemetry unit 206 or can provide signals or information to the telemetry unit via a wireless or wired connection. One example of a suitable programming unit is a computer operated by the user or clinician to send signals to the telemetry unit.

The signals sent to the processor 204 via the antenna 124 and receiver 202 can be used to modify or otherwise direct the operation of the microstimulator. For example, the signals may be used to modify the pulses of the microstimulator such as modifying one or more of pulse duration, pulse frequency, pulse waveform, and pulse strength. The signals may also direct the microstimulator to cease operation or to start operation or to start charging the battery. One advantage of a plastic housing is that plastic is typically more transparent to RF signals than metallic or ceramic materials. Thus, in some instances RF signals may be more reliably received or transmitted and received using less power or over longer distances.

Optionally, the microstimulator may include a transmitter (not shown) coupled to the processor and antenna for transmitting signals back to the telemetry unit 206 or another unit capable of receiving the signals. For example, the microstimulator may transmit signals indicating whether the microstimulator is operating properly or not or indicating when the battery needs to be charged. The processor may also be capable of transmitting information about the pulse characteristics so that a user or clinician can determine or verify the characteristics.

The optional antenna 124 can have any form. In one embodiment, the antenna comprises a coiled wire that is wrapped at least partially around the electronic subassembly within or on the plastic housing.

Any method of manufacture of the microstimulator can be used. For example, the electronic subassembly, power source, and antenna can be manufactured as described in U.S. Patent Application Publication No. 2004/0059392. These components can then be placed inside the plastic housing (or, alternatively, the plastic housing can be formed, e.g., molded, around the components). One or both of the electrodes can be formed with or attached to the plastic housing with conductors from the electronic subassembly. Coatings on the electrodes or plastic housing, if any, can be applied at appropriate points during the manufacturing process.

The microstimulator can be implanted into the body tissue using a variety of methods including surgical methods. In some embodiments, the microstimulator can be implanted using a hypodermic needle or other insertion cannula. Examples of insertion techniques can be found in U.S. Pat. No. 6,051,017.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable microstimulator, comprising:
    a plastic housing consisting essentially of plastic and having a first end and an interior surface;
    an electronic subassembly disposed within the plastic housing, wherein the interior surface of the plastic housing forms, at least in part, a surface of a cavity in which the electronic subassembly is disposed; and
    a conductive plastic electrode consisting essentially of conductive plastic and disposed at the first end of the plastic housing and in electrical communication with the electronic subassembly;
    wherein the microstimulator forms a hermetically sealed structure with the plastic housing and conductive plastic electrode hermetically sealed together.

2. The implantable microstimulator of claim 1, further comprising a second electrode disposed at a second end of the plastic housing and in electrical communication with the electronic subassembly.

3. The implantable microstimulator of claim 2, wherein the second electrode consists essentially of conductive plastic.

4. The implantable microstimulator of claim 2, wherein the plastic housing is a cylinder and the conductive plastic electrode and the second electrode are disposed at opposite ends of the cylinder.

5. The implantable microstimulator of claim 2, wherein the first and second ends are opposing ends of the plastic housing.

6. The implantable microstimulator of claim 2, wherein the plastic housing, the conductive plastic electrode, and the second electrode are metal-free.

7. The implantable microstimulator of claim 1, wherein the conductive plastic electrode is seamlessly joined to the plastic housing.

8. The implantable microstimulator of claim 7, wherein the conductive plastic electrode and plastic housing are formed together using dual material injection molding.

9. The implantable microstimulator of claim 1, wherein the plastic housing and the conductive plastic electrode comprise a same polymer material, wherein the conductive plastic of the conductive plastic electrode comprises the polymer material and a conductive material disposed in the polymer material.

10. The implantable microstimulator of claim 1, wherein the plastic housing comprises polyolefin, polypropylene homopolymer or copolymer, or polyetheretherketone.

11. The implantable microstimulator of claim 1, further comprising a coating disposed over the plastic housing.

12. The implantable microstimulator of claim 1, further comprising an antenna disposed within the plastic housing and coupled to the electronic subassembly to receive signals from an external device.

13. A method of making a microstimulator, the method comprising:
   forming a plastic housing consisting essentially of plastic and having a first end and an interior surface;
   forming a conductive plastic electrode consisting essentially of conductive plastic;
   coupling the conductive plastic electrode to the first end of the plastic housing; and
   disposing an electronic subassembly within the plastic housing, wherein the interior surface of the plastic housing forms, at least in part, a surface of a cavity in which the electronic subassembly is disposed.

14. The method of claim 13, wherein forming the plastic housing and forming the conductive plastic electrode comprises forming the plastic housing and conductive plastic electrode together.

15. The method of claim 14, wherein forming the plastic housing and the conductive plastic electrode together comprises forming the plastic housing and the conductive plastic electrode using dual material injection molding.

16. The method of claim 13, further comprising disposing a second electrode at a second end of the plastic housing.

17. The method of claim 16, wherein the second electrode consists essentially of conductive plastic.

18. The method of claim 17, wherein forming the plastic housing, forming the conductive plastic electrode, and coupling the second electrode comprises forming the plastic housing, the conductive plastic electrode, and the second electrode together.

19. The method of claim 18, wherein forming the plastic housing, the conductive plastic electrode, and the second electrode together comprises forming the plastic housing, the conductive plastic electrode, and the second electrode using dual material injection molding.

* * * * *